United States Patent [19]

Hagen et al.

[11] Patent Number: 5,000,753

[45] Date of Patent: Mar. 19, 1991

[54] THREE-PART NEUTRAL ELECTRODE FOR A HIGH FREQUENCY SURGERY DEVICE

[75] Inventors: Uwe Hagen, Forchheim; Peter Feucht, Berlin, both of Fed. Rep. of Germany

[73] Assignee: Siemens Aktiengesellschaft, Berlin and Munich, Fed. Rep. of Germany

[21] Appl. No.: 472,276

[22] Filed: Jan. 30, 1990

[30] Foreign Application Priority Data

Feb. 23, 1989 [EP] European Pat. Off. ........ 89103174.2

[51] Int. Cl.$^5$ .............................................. A61B 17/39
[52] U.S. Cl. ........................................ 606/32; 128/798
[58] Field of Search ................................. 606/32, 35; 128/639–641, 644, 798, 802, 803

[56] References Cited

U.S. PATENT DOCUMENTS

| | | | |
|---|---|---|---|
| 4,770,173 | 9/1988 | Feucht et al. | 606/32 |
| 4,807,621 | 2/1989 | Hagen et al. | 606/32 |
| 4,841,966 | 6/1989 | Hagen et al. | 606/32 |

*Primary Examiner*—Lee S. Cohen

*Attorney, Agent, or Firm*—Hill, Van Santen, Steadman & Simpson

[57] ABSTRACT

A neutral electrode for a high frequency surgery device has three planar sub-electrodes, which are arranged side by side on a carrier consisting of insulating material. To improve monitoring of the contact of the sub-electrodes with the body of the patient, the two outer sub-electrodes have substantially triangular contact surfaces, with the respective hypotenuses of the triangular contact surfaces proceeding parallel to and spaced from each other, with a central, strip-shaped sub-electrode disposed between the hypotenuses of the outer sub-electrodes. The neutral electrode is intended for use with a monitoring system which will activate an alarm if the neutral electrode becomes detached from the patient to such an extent that the danger of injury to the patient exists. This is accomplished by monitoring a current or currents flowing through the patient between sub-electrodes. The neutral electrode does not have an axis of symmetry along which a detachment of the neutral electrode from the patient could occur which would fail to cause a sufficient impedance change to trigger the alarm in time to avoid injury to the patient.

12 Claims, 1 Drawing Sheet

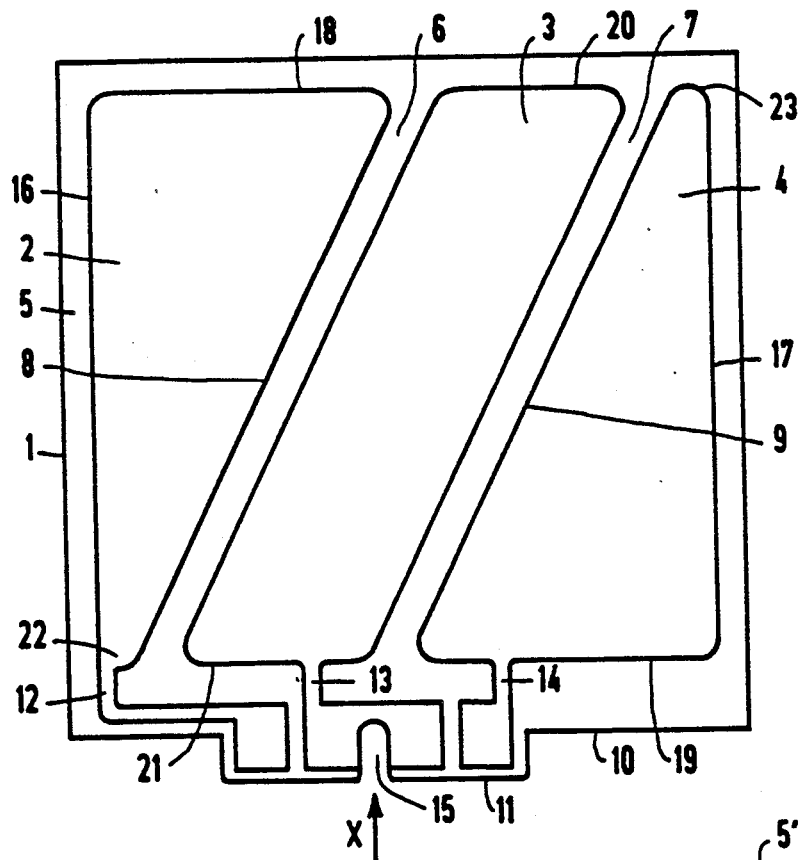
FIG 1
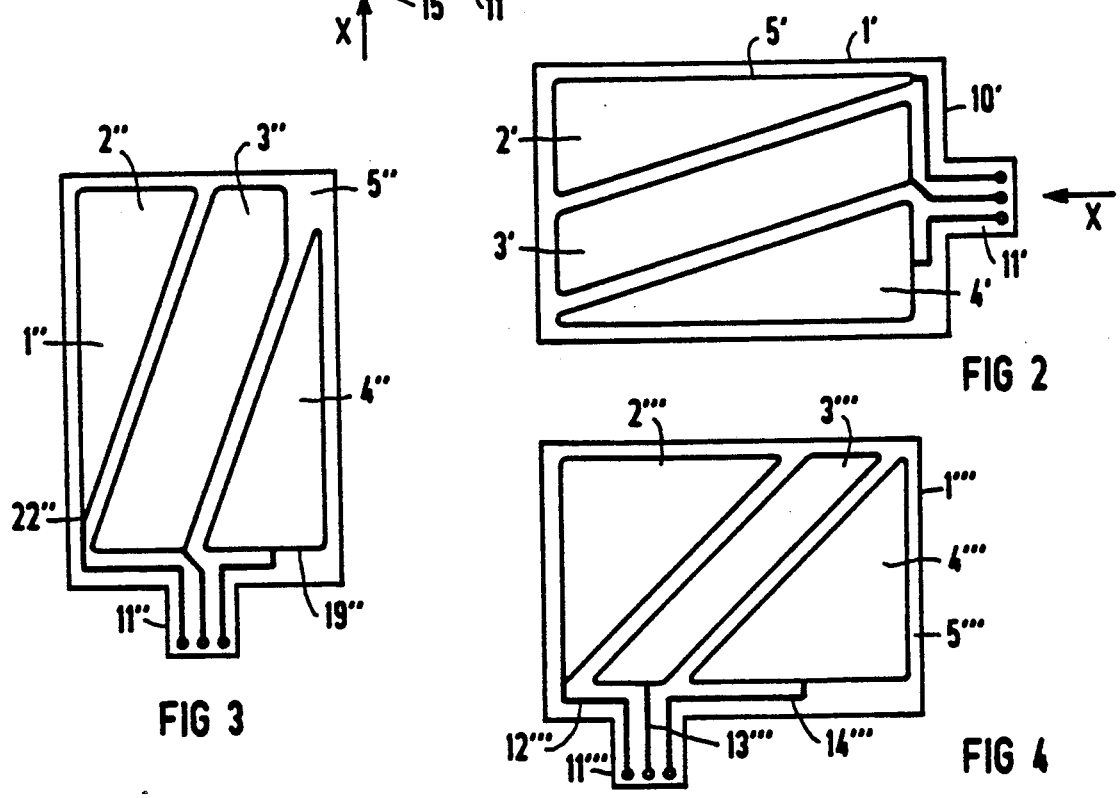
FIG 2
FIG 3
FIG 4

THREE-PART NEUTRAL ELECTRODE FOR A HIGH FREQUENCY SURGERY DEVICE

BACKGROUND OF THE INVENTION

1. Field of the Invention

The present invention is directed to a neutral electrode for a high-frequency surgery device, and in particular to such an electrode having three sub-electrodes having respective surfaces separated from each other.

2. Description of the Prior Art

A neutral electrode for a high-frequency surgery device is known from U.S. Pat. No. 4,807,621 which has three sub-electrodes arranged on a flexible carrier consisting of insulating material. In several embodiments, the sub-electrodes of this known neutral electrode are each triangular, with two of the sub-electrodes being arranged mirror symmetrically with respect to a symmetry axis, and the third sub-electrode being disposed between the mirror symmetric sub-electrodes. The mirror symmetric sub-electrodes are in the shape of right triangles, so that the combination of all three sub-electrodes results in a rectangular or square configuration. The base of the third sub-electrode proceeds substantially coincident with a line containing the respective apexes of the two right triangles. Conductor runs and terminals for connection of the neutral electrode to external circuitry are also provided on the same side of the neutral electrode on which the sub-electrode surfaces are disposed.

A further neutral electrode having three sub-electrodes is disclosed in U.S. Pat. No. 4,770,173. In this known electrode, two of the sub-electrodes are trapezoids, having edges facing each other which proceed obliquely to a predetermined direction. Another sub-electrode, having a rectangular shape, is disposed in the predetermined direction following the two trapezoidal sub-electrodes. Insulating strips are disposed between the sub-electrodes.

Another neutral electrode arrangement is disclosed in German OS 35 44 443, corresponding to U.S. Pat. No. 4,754,757. This neutral electrode has three sub-electrodes, each of which is rectangular in shape, with the sub-electrodes being disposed parallel to each other on a carrier. A circuit is also disclosed therein for monitoring the surface contact of the neutral electrode with the body of a patient during operation of a high-frequency surgery device. In such high-frequency surgery, misapplication or detaching of the neutral electrode may cause an injurious burn to the patient. A neutral electrode having a plurality of sub-electrodes is therefore provided, connected to a monitoring unit, to trigger an alarm signal to the surgeon as the neutral electrode is becoming detached, but preferably before the neutral electrode becomes detached to such an extent to cause injury to the patient. For this purpose, an auxiliary test current is conducted from a current source to one of the sub-electrodes, through the patient, and returned via another sub-electrode to the test current source. This current is monitored, such as by detecting any changes in impedance. When this circuit is closed, it is insured that each sub-electrode is pressed against the patient with substantially its entire surface, so that the full high-frequency operating current can be applied.

In these known neutral electrodes, however, the arrangement of sub-electrodes unintentionally permits a partial detachment of the sub-electrodes from the surface of the patient without the monitoring circuit responding and thus without the alarm being actuated. This sometimes results in the alarm being triggered too late to avoid injury to the patient. This is because the monitoring circuit reacts differently depending upon the direction of detachment of the neutral electrode from the surface of the patient. It is possible in these known neutral electrodes for the electrode to become partially detached from the body of the patient along a symmetry line so that the changes in impedance between respective pairs of sub-electrodes also change symmetrically, so that an overall impedance difference does not occur, as is necessary to trigger the alarm.

Due to the electrical conductance of the patient tissue, which varies from patient to patient, a resistance or capacitance between two sub-electrodes of a neutral electrode does not, but itself, provide a reliable indicator as to whether contact between the patient and the neutral electrode is sufficient to avoid burning the patient. If, for example, the tissue of one patient has a third of the tissue resistance of another patient, approximately a third of the electrode surface may suffice to meet a preset limit value for the test current given this low tissue resistance. For this reason, the aforementioned neutral electrodes having a plurality of sub-electrodes were devised so that the respective currents between various pairs of sub-electrodes can be measured to determine if detachment has occurred to such an extent to place the patient in danger of being injured. For this purpose, an auxiliary test current can be used, or the high-frequency surgery current. It is assumed that if the currents between the respective pairs of sub-electrodes remain symmetrical, detachment has not occurred. As noted above, however, the known neutral electrodes can become detached from the surface of a patient along a line of symmetry, so that symmetrical test currents are still measured, even though detachment has occurred.

SUMMARY OF THE INVENTION

It is an object of the present invention to provide a neutral electrode having three sub-electrodes which minimizes the likelihood of symmetrical test currents being measured as the neutral electrode becomes detached from a patient.

It is also an object of the present invention to provide such a neutral electrode which can be easily manufactured.

It is another object of the present invention to provide such a neutral electrode which insures a good contact with the patient.

The above objects are achieved in accordance with the principles of the present invention in a neutral electrode wherein the two outer sub-electrodes have substantially triangular contact surfaces, with the respective hypotenuses of the outer sub-electrodes proceeding parallel to and spaced from each other, with a central strip-shaped sub-electrode disposed between the hypotenuses.

The neutral electrode disclosed herein has no detachment (i.e., bisecting) symmetry line along which a detachment of the electrode from the body of a patient would be possible without an alarm being actuated by a monitoring circuit connected to the neutral electrode which undertakes measurements (e.g. impedance measurements) between the sub-electrodes. In known neutral electrodes, the possibility of detachment occurring without an alarm being triggered resulted from the possibility of detachment occurring in such a manner that the impedance changes between the various sub-electrode pairs would be substantially the same, therefore symmetrical test currents would still be measured, with no impedance difference being detected. In the neutral electrode disclosed herein, detachment in a manner which maintains symmetrical test currents is highly unlikely.

For monitoring the impedance between the sub-electrodes in the neutral electrode disclosed herein, the central sub-electrode, or one of the outer sub-electrodes can be selected as a feed-in electrode for the test current used for the impedance measurement.

With the arrangement of the sub-electrodes in the neutral electrode disclosed herein, the unintended detachment of a sub-electrode surface from the patient will in almost all instances not occur along a line of symmetry of the remaining sub-electrode areas, particularly if it is assumed that the detachment occurs along a straight line and that the straight line is parallel to one of the outside edges of the neutral electrode. It is conceivable, however, that detachment of the neutral electrode disclosed herein could occur along a straight line which would result in approximate symmetry of the remaining areas being maintained, however, this could only occur along a detachment line proceeding obliquely to the outer edges of the electrode, and with increasing detachment the angle of the line of detachment would continuously change relative to the outer edges of the electrode so that the areas remaining in contact with the patient would rapidly become unsymmetrical, thereby triggering the alarm.

The neutral electrode disclosed herein can be used wherein only the current relationship between the two triangular outside sub-electrodes is monitored with the central sub-electrode serving for feeding-in an auxiliary current.

The circuit connection for the neutral electrode is structured so that a connection can only be made with a compatible plug leading to the high-frequency surgery device. This insures that the proper electrode is connected to the high-frequency surgery device so that an incorrect accessory connection can not occur.

DESCRIPTION OF THE DRAWINGS

FIG. 1 is a plan view of a neutral electrode constructed in accordance with the principles of the present invention in a first embodiment.

FIG. 2 is a plan view of neutral electrode constructed in accordance with the principles of the present invention in a second embodiment.

FIG. 3 is a plan view of a neutral electrode constructed in accordance with the principles of the present invention in a third embodiment.

FIG. 4 is a plan view of a neutral electrode constructed in accordance with the principles of the present invention in a fourth embodiment.

DESCRIPTION OF THE PREFERRED EMBODIMENTS

As shown in FIG. 1, a neutral electrode 1 for a high-frequency surgery device has three planar sub-electrodes 2, 3 and 4, which are arranged on an elastic carrier 5 so that the sub-electrodes are separated from each other by insulating or isolating strips 6 and 7, or by strips of low electrical conductivity. The sub-electrodes 2, 3 and 4 are arranged side by side with respect to a predetermined direction x, e.g. in the application direction of the electrode. The two outer sub-electrodes 2 and 4 are formed as triangles having respective hypotenuses 8 and 9. The hypotenuses 8 and 9 proceed obliquely relative to the direction x, and are parallel to each other. The third sub-electrode 3 is centrally disposed between the hypotenuses 8 and 9, and is strip-shaped. The sub-electrodes consist of an electrically conductive foil, e.g. a metal foil or a metal net, and are fastened on the flexible carrier 5. The carrier 5, which is preferably self-adhesive and may consist of rubber of plastic, is in the shape of a square in the embodiment of FIG. 1. At its edges, the carrier 5 projects beyond the sub-electrodes 2, 3 and 4. A terminal connection 11 is provided on the side 10 of the carrier 5 on which the sub-electrodes are disposed. The terminal connection 11 has terminal paths respectively connected to connecting lines 12, 13 and 14 leading respectively to the sub-electrodes.

The terminal connection 11 is shaped so that it can only be coupled with a compatible plug (not shown) of an appliance cord for a high-frequency surgery device. This insures that the neutral electrode 1 will not be connected to an incorrect cord, and that the proper neutral electrode cord will not be connected to an incorrect accessory. This is accomplished by a notch 15 of predetermined shape and location which provides a mechanical keying code.

As shown in FIG. 1, the arrangement and shape of the sub-electrodes is such that the longer sides 16 and 17 of the outer sub-electrodes 2 and 4 basically determine the length of the electrode 1 in the x-direction. The shorter sides 18 and 19 of the sub-electrodes 2 and 4 are respectively aligned with the edge 20 and 21 of the central sub-electrode 3 on a line which also contains the respective apexes 22 and 23 of the outer sub-electrodes 2 and 4.

A rectangular embodiment of an electrode 1' is shown in FIG. 2 wherein a terminal connection 11' is disposed at one of the shorter sides 10'0 of the carrier 5'. The sub-electrodes 2', 3' and 4' are arranged one above the other along the x-direction.

In the embodiment of FIG. 3, the outer sub-electrodes 2" and 4" are right triangles, and the strip-shaped central sub-electrode 3" is slightly shortened at one corner so that the sub-electrode 3" has five sides. It is also possible to make a mirror symmetric shortening of the corner of the sub-electrode 3" at the lower left of FIG. 3, in which case the sub-electrode 3" would have six sides.

In the embodiment of FIG. 4, the sub-electrodes 2''' and 4''' are equilateral right triangles. In order to make the connecting line 12''', 13''' and 14''' from the respective sub-electrodes to the terminal connection 11''' of approximately equal length, the terminal connection 11''' is disposed off-center at an edge of the carrier 5''' of the neutral electrode 1'''.

In all of the above embodiments, the outer electrodes have been shown for exemplary purposes as congruent right triangles, however, it will be understood that it is not necessary that the triangles be right triangles, and the outer electrodes may, for example, be congruent acute triangles.

All of the above embodiments have in common that the conductive surface area of the neutral electrode remains substantially constant across the length of the electrode perpendicular to the x-direction. This improves the capacitance measurement for monitoring the neutral electrode for insuring proper attachment of the electrode to the body of the patient. The capacitance measuring system may include a unit to detect whether the measured contact area between the neutral electrode and the patient is greater than a defined value which is the minimum surface area necessary for safe operation of the high-frequency surgery device. Instead of a capacitance measurement, however, a measurement as disclosed in the aforementioned U.S. Pat. No. 4,807,621 may be made. As disclosed therein, a measurement of the partial currents between the sub-electrodes of the neutral electrode is made and an alarm signal is generated if one of the partial currents becomes larger than the other by a predetermined amount. If a substantially equal current distribution between the sub-electrodes is measured, injury to the patient by burning should not occur, and the alarm signal will not be actuated. If one of the partial currents becomes larger than the other by a predetermined amount, the alarm will be triggered.

Although modifications and changes may be suggested by those skilled in the art, it is the intention of the inventors to embody within the patent warranted hereon all changes and modifications as reasonably and properly come within the scope of their contribution to the art.

We claim as our invention:

1. A neutral electrode for use with a high-frequency surgery device, said neutral electrode comprising:
   a carrier consisting of electrically insulating material and having a surface adapted for contact with a patient;
   first and second sub-electrodes disposed on said surface of said carrier, said first and second sub-electrodes each being substantially triangular and each having a side facing the other of said first and second sub-electrodes, said facing sides being spaced from and parallel to each other; and
   a third sub-electrode centrally disposed between said facing sides of said first and second sub-electrodes, said third electrode being strip-shaped.

2. A neutral electrode as claimed in claim 1, wherein said first and second sub-electrodes are congruent triangles arranged on said surface of said carrier relative to said third sub-electrode so that said first, second and third sub-electrodes in combination form a rectangle.

3. A neutral electrode as claimed in claim 1, wherein said first and second sub-electrodes are congruent triangles arranged on said surface of said carrier relative to said third sub-electrode so that said first, second and third sub-electrodes in combination form a square.

4. A neutral electrode as claimed in claim 1, wherein said first and second sub-electrodes are right triangles and wherein said facing sides are the hypotenuses of said right triangles, and wherein said third sub-electrode has oppositely disposed narrow sides, each narrow side being . aligned with a side of one of said right triangles so that said first, second and third sub-electrodes in combination form a rectangle.

5. An electrode as claimed in claim 4, wherein said third sub-electrode has at least one end which is shortened and consists of two sides of said third sub-electrode so that said third sub-electrode has at least five sides.

6. A neutral electrode as claimed in claim 1, wherein said first and second sub-electrodes are right triangles and wherein said facing sides are the hypotenuses of said right triangles, and wherein said third sub-electrode has oppositely disposed narrow sides, each narrow side being aligned with a side of one of said right triangles so that said first, second and third sub-electrodes in combination form a square.

7. An electrode as claimed in claim 6, wherein said third sub-electrode has at least one end which is shortened and consists of two sides of said third sub-electrode so that said third sub-electrode has at least five sides.

8. A neutral electrode as claimed in claim 1, wherein said carrier has a terminal separately electrically connected to each of said first, second and third sub-electrodes and adapted for connecting said neutral electrode to a high-frequency surgery device, said terminal disposed at one side of said carrier, and wherein said first and second sub-electrodes are acute triangles, said third sub-electrode has oppositely disposed short sides, with one of said short sides being co-linear with a side of said first sub-electrode and an apex of said second sub-electrode, and the other of said short sides of said third sub-electrode being co-linear with an apex of said first sub-electrode and a side of said second sub-electrode.

9. A neutral electrode as claimed in claim 1, wherein said first and second sub-electrodes are equilateral right triangles.

10. A neutral electrode as claimed in claim 1, wherein said carrier has a terminal connection separately electrically connected to each of said first, second and third sub-electrodes and adapted for electrically connecting sad neutral electrode to a high-frequency surgery device having a plurality of electrical connections, said terminal connection having a mechanical key permitting a unique connection of said neutral electrode with only one of sd plurality of electrical connections.

11. A neutral electrode as claimed in claim 10, wherein said terminal connection is formed by a projection on said carrier, and wherein said mechanical key is a notch of a selected size and at a selected location in said projection.

12. A neutral electrode as claimed in claim 10, wherein said terminal connection is disposed off-center at a side of said carrier.

* * * * *